United States Patent [19]
Cook et al.

[11] 4,001,700
[45] Jan. 4, 1977

[54] DIGITAL WAVEFORM GENERATOR FOR AUTOMATIC RESPIRATORY VENTILATORS

[75] Inventors: Albert M. Cook; Frank A. Engleman, Jr.; James G. Simes, all of Sacramento, Calif.

[73] Assignee: Sutter Hospitals Medical Research Foundation, Sacramento, Calif.

[22] Filed: Apr. 16, 1974

[21] Appl. No.: 461,303

[52] U.S. Cl. .................. 328/129; 328/72; 128/145.5; 128/DIG. 17; 340/347 DA

[51] Int. Cl.² ............. A03K 13/02; H03K 21/18; A61H 31/00

[58] Field of Search ......... 128/145.5, 145.6, 145.8, 128/DIG. 17; 328/72, 129, 130, 73, 75, 48; 340/347 DA

[56] References Cited
UNITED STATES PATENTS

| | | | |
|---|---|---|---|
| 3,629,710 | 12/1971 | Durland | 328/48 X |
| 3,668,529 | 6/1972 | Meyer | 328/129 |
| 3,725,794 | 4/1973 | Asplund | 328/129 |
| 3,805,167 | 4/1974 | Nash et al. | 328/48 X |
| 3,873,815 | 3/1975 | Summers | 328/48 X |
| 3,911,899 | 10/1975 | Hattes | 128/145.8 X |

Primary Examiner—John S. Heyman
Attorney, Agent, or Firm—Christie, Parker & Hale

[57] ABSTRACT

A digital system for use in controlling the cycling of a respirator includes a digital clock for dividing each respiratory cycle (inspiration and expiration) into a fixed number of counts. A respiratory rate circuit is adjusted to vary the frequency of the counts to define the total time of each respiratory cycle (in breaths per minute). A respiration ratio circuit is independently adjusted to control the ratio of inspiration time to expiration time for each respiratory cycle by selecting a fixed number of counts to define a desired inspiration time. The remaining counts define expiration time. A digital-to-analog converter is driven in response to the counters to produce a voltage output defining a desired volume-versus-time waveform having the previously selected rate and ratio. The output from the digital-to-analog converter controls the cycling of a volume-cycled respirator. Read-only-memories may be inserted between the counters and the input to the digital-to-analog converter to generate a large number of different inspiration waveforms.

31 Claims, 11 Drawing Figures

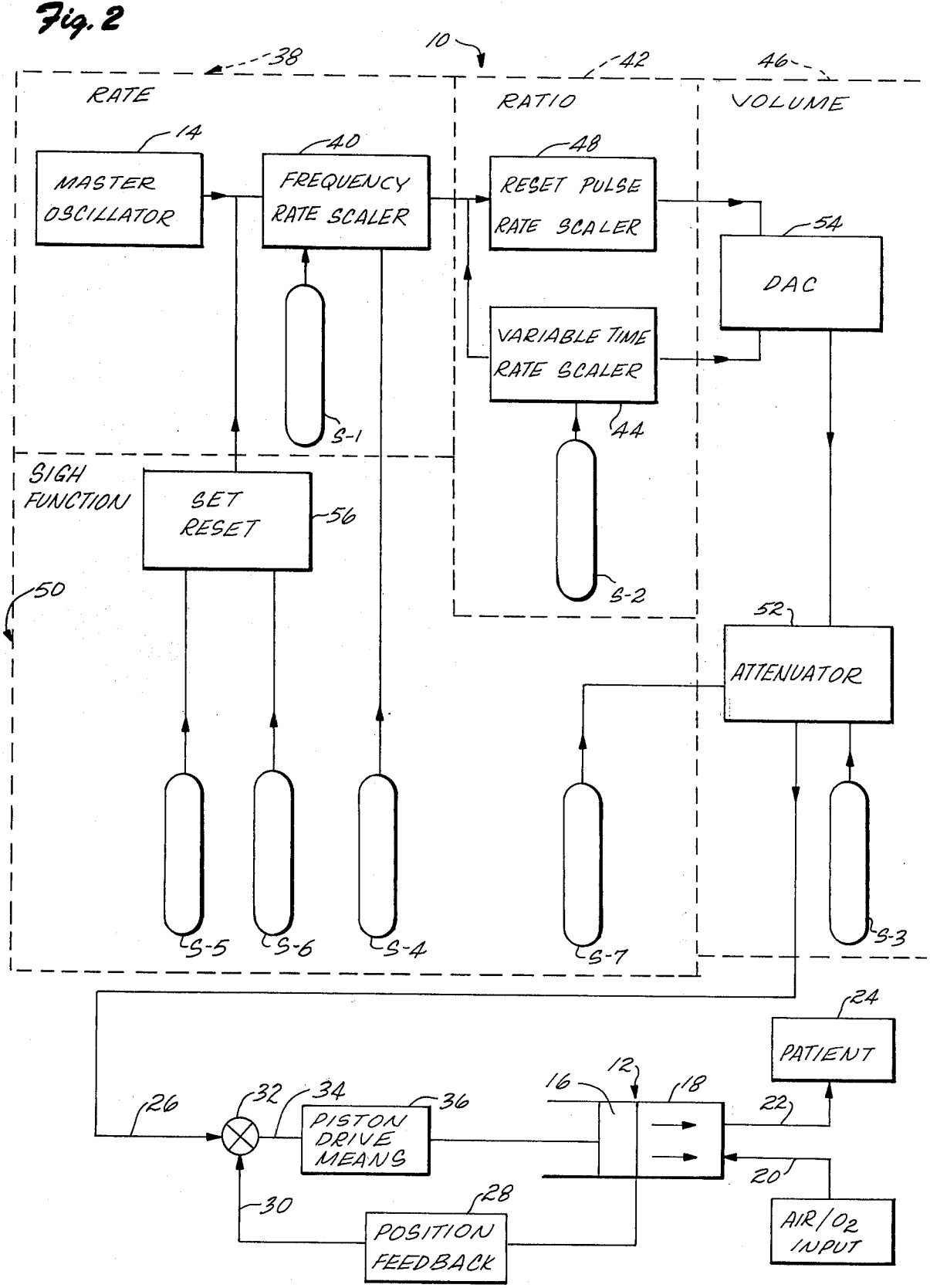

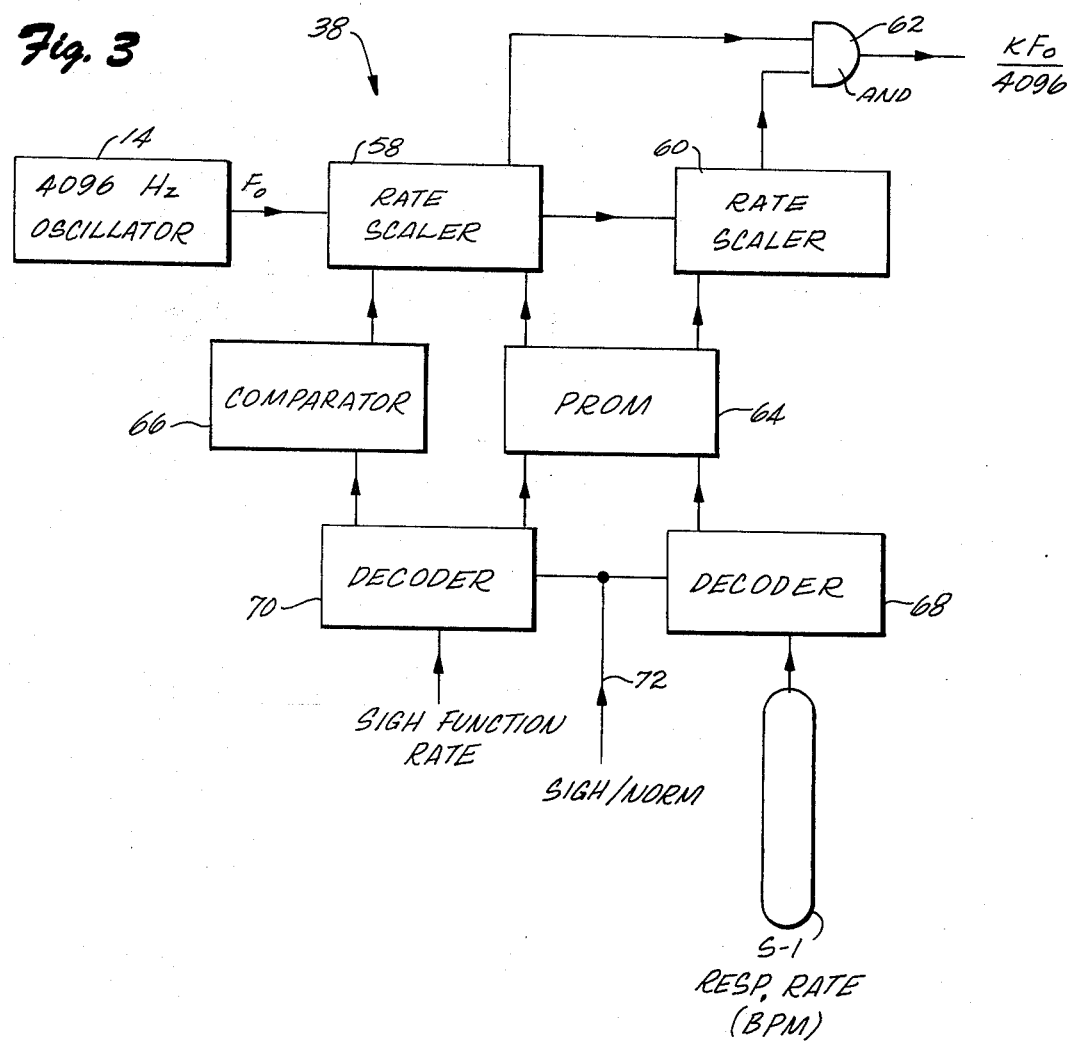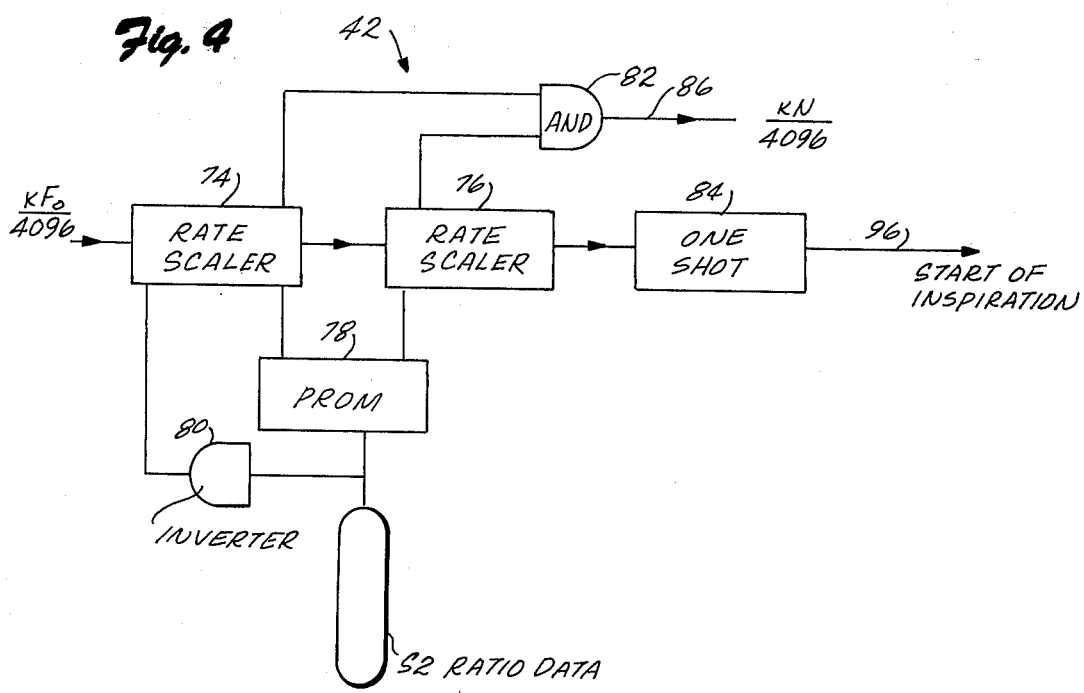

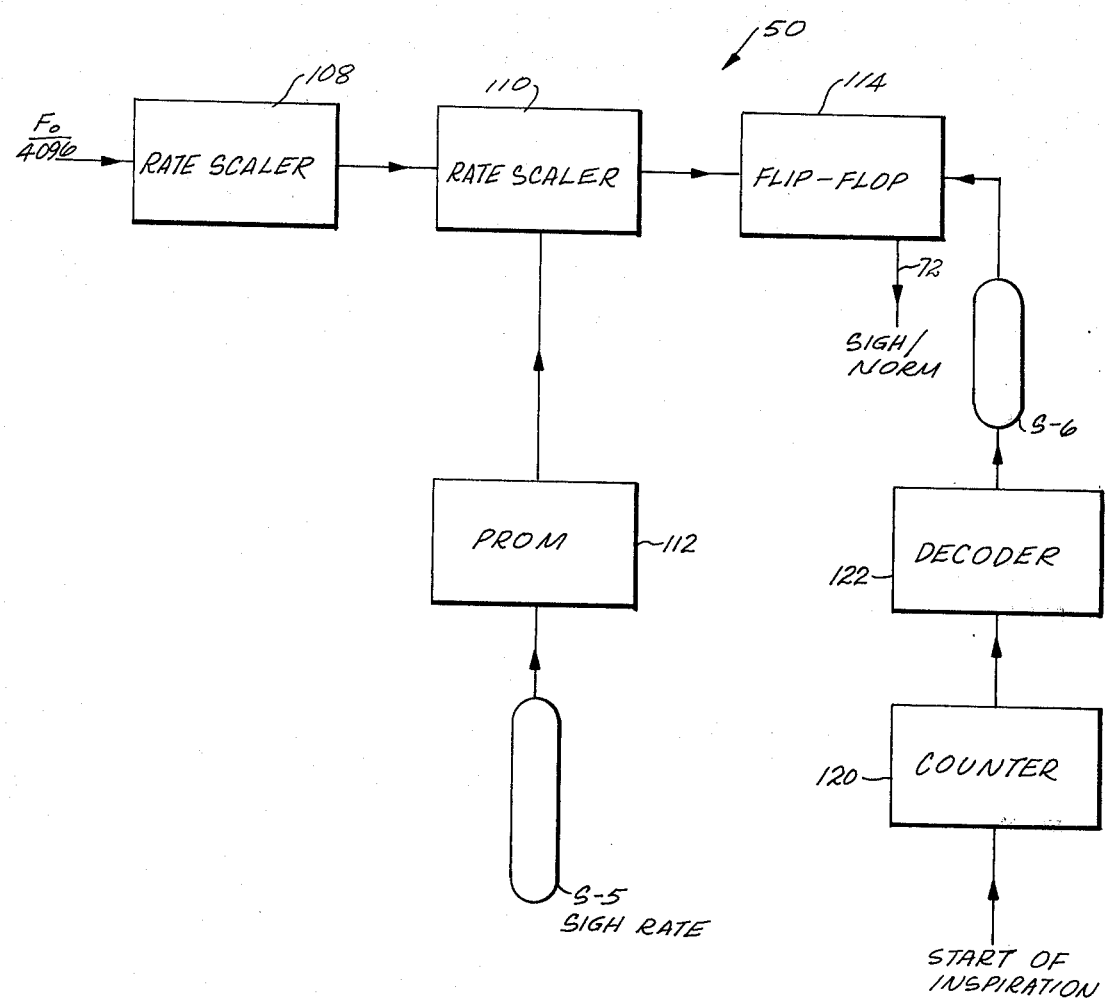

# DIGITAL WAVEFORM GENERATOR FOR AUTOMATIC RESPIRATORY VENTILATORS

BACKGROUND

This invention relates to respirator therapy, and more particularly to a digital waveform generator for use in controlling the cycling of an automatic respiratory ventilator.

Respiratory therapy uses various devices for automatic ventilation of the lungs. These devices are typically used for either short-term assist, or prolonged artificial respiration. Since they substitute for the entire respiratory system, the devices designed for long-term mechanical respiration must serve several functions. Foremost of these is "ventilation," i.e., supply of oxygen and removal of carbon dioxide. This function is directly related to perfusion of the tissues of the body with oxygen and removal of carbon dioxide. Since long-term ventilation requires a tracheostomy (an artificial opening in the trachea), the functions of the nose (humidification and heating of incoming air) also must be provided.

Mechanical ventilation differs in one main respect from normal respiration. In artificial ventilation, the air is supplied by applying a positive pressure at the mouth, or tracheostomy, while in normal respiration, air is drawn in by a negative pressure inside the thorax. This difference leads to a number of undesirable effects of mechanical ventilation primarily involving the cardiovascular system. In particular, cardiac output may be reduced under certain flow conditions. It has been shown that the particular volume-time waveform, which is used during inspiration, may result in different effects on the cardiopulmonary system. A decelerating flow pattern, for example, has a lower peak pressure in the upper airways and in the alveoli, and a corresponding smaller effect on the respiratory system. An accelerating flow pattern, on the other hand, has a lower mean pressure and a smaller effect on cardiac output.

Several methods of classification of ventilators have been proposed. The most widely used method is based on the manner in which the changeover from inspiration to expiration is controlled. Three types are distinguished: pressurecycled, volume-cycled, and time-cycled. In each case, the changeover occurs when a preset pressure, volume, or inspiration time is reached. Less widely used classifications include: specification based on the "stability" or "flexibility" of minute volume, tidal volume and inspiratory flow in the face of changing patient resistance and compliance, and functional analysis of ventilators based on the power and force supplied. Some of the additional controls found on ventilators include respiratory rate, inspiratory flow rate, tidal volume, minute ventilation, and ratio of inspiration time to expiration time.

Electronic control has been used on ventilators in varying degrees in recent years. Of the 81 ventilators listed in Mushin et al. *Automatic Ventilation of the Lungs*, 2d ed., Oxford Blackwell, 1969, 15 ventilators use some means of electronic control. In most cases, electronic control is implemented to provide more accurate and repeatable control signals than gas-powered or electro-mechanical ventilators. One group of electronically controlled ventilators includes devices which determine respiration rate and ratio by varying both inspiration and expiration time. This approach is unsuitable from an engineering point of view since there is interaction between controls, and from an operator's point of view because the controls are ambiguous. For example, if one adjusts inspiratory time and expiratory time, it is possible to obtain a clinically invalid ratio of less than 1:1. Another group of ventilators have no ratio control. The ratio is derived from other controls, generally rate, tidal volume, and inspiratory flow rate. In some cases, either inspiratory or expiratory time is adjusted rather than rate. In either case, invalid ratios can be obtained and the actual ratio is unknown unless appropriate monitoring is available. A third group of ventilators provide a direct setting for respiratory rate and ratio. However, ventilators in this group, and the other groups discussed above, have not had the combined independence of controls, stability of operation for variations in patient resistance and compliance, and overall accuracy of all controls characteristic of the present invention.

SUMMARY

This invention provides a digital waveform generator for use in controlling the cycling of a respirator. The digital system includes a digital clock for dividing each respiratory cycle (defined by inspiration time plus expiration time) into a fixed number of counts. An adjustable respiratory rate circuit varies the frequency of the counts to define the total time of each respiratory cycle. A respiration ratio circuit is adjustable independently of the rate circuit for controlling the ratio of inspiration time to expiration time for each respiratory cycle. Preferably, ratio is controlled by producing fixed number of counts to define a desired inspiration time. The remaining counts in the respiratory cycle define the expiration time. The counts from the rate and ratio circuits drive a digital-to-analog converter for producing an output defining a desired volume-versus-time waveform having the previously selected respiratory rate and ratio. The output from the digital-to-analog converter controls the cycling of a respirator.

Thus, the respiration ratio of the respirator is easily adjusted independently of respiratory rate. Moreover, read-only-memories, or other similar waveform generators, may be inserted between the digital-to-analog converter and the rate and ratio counters to generate a variety of different inspiration waveforms. Thus, the tidal volume adjustment is also independent of the other controls.

These and other aspects of the invention will be more fully understood by referring to the following detailed description and the accompanying drawings.

DRAWINGS

FIG. 2 is a schematic block diagram illustrating the digital waveform generator of this invention used with a feedback control system for controlling movement of a respirator piston;

FIG. 3 is a schematic block diagram illustrating a respiratory rate circuit of this invention;

FIG. 4 is a schematic block diagram illustrating a respiration ratio circuit of this invention;

FIG. 5b is a partial schematic block diagram illustrating an alternative embodiment of the volume signal generating circuit of FIG. 5a; and FIG. 6 is a schematic block diagram illustrating a sigh function circuit of this invention.

DESCRIPTION

FIG. 2 illustrates a digital system 10 for generating a desired volume-versus-time waveform for controlling the cycling of a respirator 12. The basic principle of the digital system is that every respiratory cycle (inspiration plus expiration time) is divided into a fixed number of counts established by a master oscillator 14 shown in FIGS. 2 and 3. The oscillator 14 provides a stable time base on which to base the control of the various input parameters of the digital system. Respiration ratio is controlled by selecting a variable time interval from the fixed time of the entire respiration cycle. The chosen time interval is designated as inspiration time. The remaining time of the total respiratory cycle then becomes the expiration time. Respiratory rate is adjusted by varying the total time of each respiratory cycle. Thus, the ratio of the system is adjusted independently of the rate.

Figure 1A:
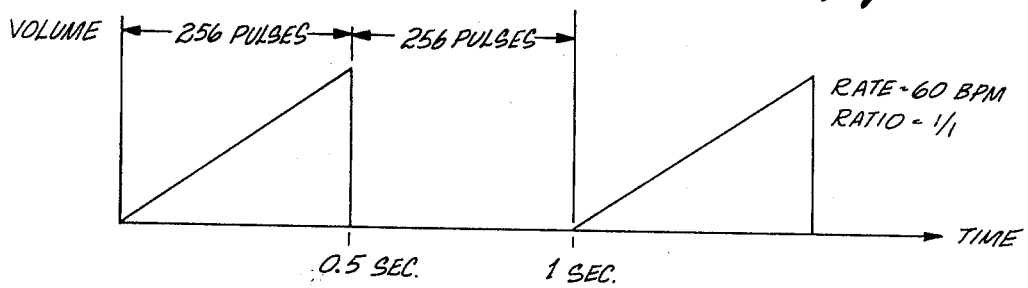
FIGS. 1a through 1e illustrate a variety of volume-versus-time waveforms generated by the digital system of this invention.
Figure 1B:
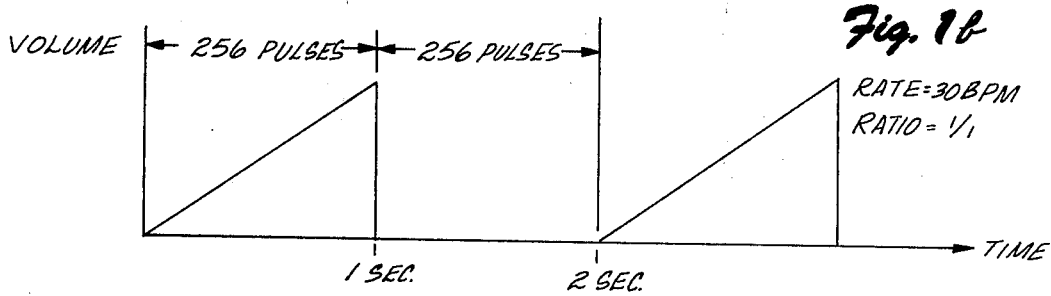
Figure 1C:
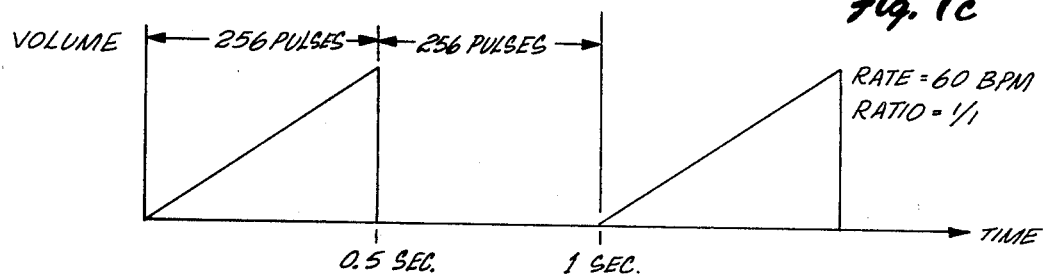
Figure 1D:
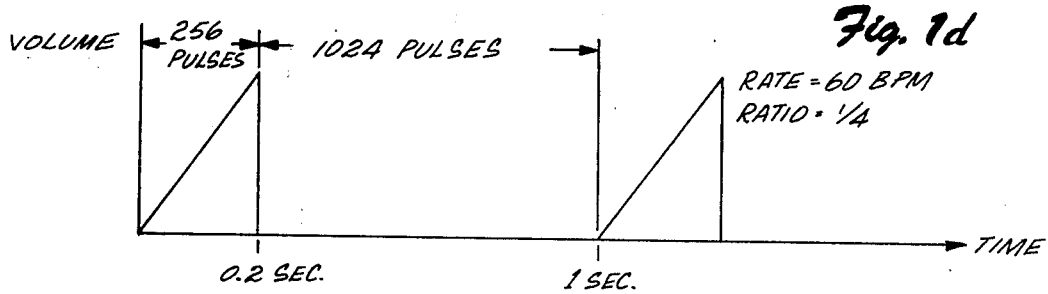

Examples of the independent control of rate and ratio are illustrated in FIGS. 1a through 1e. In FIGS. 1a and 1b, the respiration ratio is held at 1/1 and the time interval is increased from one second to two seconds. In FIGS. 1c and 1d, the respiration time cycle is kept constant at one second and the ratio is changed from 1/1 to ¼. In all instances, the adjustment of one variable, rate or ratio, does not affect the other.

FIG. 2 is a block diagram which illustrates the implementation of the basic principles of the digital system. The digital system is used as a waveform generator for controlling the cycling of a linear driven piston or concertina bag device providing air to a patient. The system in FIG. 2 illustrates the use of the system for controlling the respirator 12 which includes a piston 16 disposed in a cylinder 18. The piston is driven back and forth in the cylinder by suitable drive means, preferably a translational motor such as a linear actuator, or a linear induction motor, coupled to the piston by appropriate means.

A line 20 delivers a supply of gas, usually air or a suitable mixture of air and oxygen, to the interior of the piston cylinder. When the piston drive pushes the piston forward in the direction of the arrows shown in FIG. 2, gas admitted through the line 20 is forced out of the piston cylinder through suitable valves (not shown) and through a line 22 connected to a patient (represented schematically at 24) in a conventional manner so as to deliver the gas to the patients's lungs. The reciprocating movement of the piston periodically pumps the gas into the patient's lungs to simulate the inspiratory cycle of normal breathing and allow suitably adjusted time for expiration. The expiratory cycle occurs each time the piston is retracted, with the patient exhaling passively through a separate conduit (not shown), or with expiratory assist devices or retard devices (not shown) as is well known in the art of respiratory therapy.

This invention provides means for generating a desired volume-versus-time waveform for use in controlling movement of the piston 16 to deliver a controlled volume of gas to the patient 24 throughout each respiratory cycle. The waveform generator 10 receives input data which influence the time-related volume of gas to be delivered during inspiration. The waveform generator 10 produces a voltage signal or reference output 26 proportional to the desired volume of gas to be delivered to the patient as a function of time. The output of signal 26 is a voltage which is varying during inspiration time. During expiration time this voltage is reduced to zero volts. The position of the piston is proportional to the voltage applied. In this manner, the system provides a volume-versus-time drive signal.

The position of the piston is accurately controlled by a closed loop feedback system which continuously adjusts the position of the piston 16 so as to maintain the desired flow of gas represented by the waveform output signal 26. The feedback control system includes a suitable transducer 28 for measuring the system's control variable, which is preferably the volume of gas actually delivered to the patient as a function of time. Alternatively, the transducer 28 can measure the volume of gas remaining in the cylinder. Preferably, the transducer is a position transducer which determines the instantaneous and actual position of the piston within the cylinder and produces a corresponding output or a position feedback signal 30 proportional to the actual volume of gas delivered by the piston. The feedback control system also includes means represented by a summing junction 32 for comparing the desired position signal 26 with the feedback signal 30 to produce a position error signal 34 representing the deviation between the desired volume and the actual volume of gas delivered to the patient as a function of time. The position error is fed to a piston drive 36 for continuously adjusting the position of the piston to maintain the desired volume-time flow of gas from the piston to the patient.

It can be seen from FIG. 2 that the system consists of four major blocks or functions. A rate block 38 includes the master oscillator 14, a frequency rate scaler 40, and an operator control S-1. The master oscillator provides a stable reference frequency for all the control functions. The rate scaler 40, in conjunction with the operator control S-1, provides the proper frequency input for a ratio block 42. The ratio block includes a variable time rate scaler 44 controlled by an operator switch S-2. The rate scaler 44 provides the variable time required for a volume block 46 to develop an independent ratio. The ratio block 42 also includes a rate scaler 48 which is a fixed divider providing a "reset" pulse to the volume block 46 and a "sigh function" block 50 for indicating the completion of a respiratory cycle and the start of a new cycle. It will be shown more clearly below that the two rate scalers 44 and 48 provide the required independence of respiratory rate and ratio.

The volume block 46 provides operator adjustment of the analog drive signal 26 through the use of an attenuator 52 operating on the output of a digital-to-analog converter (DAC) 54. This adjustment is independent of all others.

The sigh function block 50 includes a set-reset circuit 56 for overriding the normal respirator functions when an artificial "sigh" is desired. The sigh function block provides operator control of sigh rate, sigh/hour, sigh/interval, and sigh volume through use of switches S-4 through S-7, respectively. The sigh function block 50 is interconnected with the rate block 38 and the volume block 46 using several of the same components to reduce overall system complexity.

FIG. 3 shows the detailed arrangement of the rate circuit 38, which includes eight integrated circuits. The master oscillator 14 is a 4096 Hz oscillator for generating a fixed train of signals or timed pulses. The frequency output from the oscillator 14 is fed to a pair of rate scalers 58 and 60. A rate scaler is a device which provides an output frequency proportional to preset inputs. If the input frequency is equal to the proportionality constant built into the scaler, the output will equal the present inputs. In this case, by cascading rate scalers 58 and 60, the built- in proportionality constant becomes K/4096, and the output of the rate scalers is equal to the input multiplied by this proportion. When the input is equal to 4096 Hz, K/4096 becomes simply "K" Hz. Since the range of respiratory rate provided by the system is 1 to 60 breaths per minute (BPM), a rate of 60 BPM is set to correspond to "K" = 4096 Hz. In this manner, 30 BPM becomes 2048 Hz, 15 BPM becomes 1024 Hz, etc. By choosing the frequencies in this manner, it is possible to provide respiratory rates of between 1 to 60 BPM in steps of one cycle.

Rate scalers 58 and 60 also provide a second output which is proportional to $F_0/4096$, or 1 Hz. The outputs from the rate scalers are fed to an AND gate 62 for summing the outputs of the rate scalers.

In order to provide clinically meaningful controls for the operator while generating the proper "K" number for the rate scalers, an interface is provided by a programmable read-only-memory (PROM) 64. It is desirable to have the operator set the rate switch S-1 to a number such as 30 BPM, rather than 2048 Hz. The PROM 64, together with a comparator 66 and switch S-1, accomplish this function. S-1 is an operator controlled thumbwheel switch, labeled 1 to 60 BPM, that provides a binary coded decimal (BCD) output through a pair of sigh function decoders 68 and 70 to the PROM 64 and the comparator 66. The purpose of decoders 68 and 70 is to allow the use of the rate scalers in circuit 38 when a sigh function is required. The PROM 64 converts the BCD switch commands to the "K" numbers required by the rate scalers 58 and 60. The outputs of the memory are connected to the preset inputs of the rate scalers. The comparator 66 in effect lengthens the memory to nine bits instead of eight. The method of operation is that BCD data corresponding to specific rates from the operator switch S-1 addresses the PROM 64. The "K" codes stored at the appropriate memory locations in the PROM are used to control the rate scalers.

The rate input from switch S-1 can be overridden by the sigh/normal control signal 72 from the sigh function circuit 50. Decoders 70 connect the rate data from the sigh function block 50 to the PROM 64. The decoders 68 and 70 convert from BCD to binary. The additional codes for the sigh override are stored in the PROM, so that the proper "K" numbers are also available for sigh operation.

FIG. 4 shows the circuit 42 which provides operator control of respiratory ratio. The circuit is similar to the rate circuit in that it uses rate scalers 74 and 76 and a PROM 78. The PROM decodes the operator ratio settings of switch S-2 and provides the proper codes to the preset inputs of the rate scalers 74 and 76. An integrated circuit package contains an inverter 80 for serving as a ninth bit for the PROM 78, and an AND gate 82 for cascading the rate scalers 74 and 76. The rate scalers 74 and 76 also have the property of providing dual outputs. These rate scalers are used to deliver a fixed output pulse and a variable output for adjusting the duration of the pulses which define inspiration time. The fixed output is always equal to K/4096. A one-shot 84 is used to provide a uniform pulse width independent of frequency. This pulse is generated at the beginning of each inspriation phase. At "K" = 4096 (60 BPM), the fixed pulse output is 1 Hz. At "K" = 2048 (30 BPM), the fixed pulse output of 0.5 Hz. In this manner, a pulse is provided at the start of inspiration regardless of the respiratory rate setting.

The variable ratio control portion of the circuit 42 provides a variable output (KN)/4096 proportional to the preset input settings. The "K" input is provided by the rate circuit 38 and is multiplied by the factor N/4096. If the "K" input is 4096 (60 BPM), the output will be "N". If the "K" input is 2048 (30 BPM), the output is 0.5 "N". In a like manner, all rate settings will appear as a fractional "N" output. The "N" output required is determined by the ratio desired and the fixed requirements of volume circuit 46. The volume circuit is designed so that 256 pulses on the KN/4096 input line 86 determine the inspiration phase. Therefore, from FIG. 1a, if "N" = 512 (ratio = 1/1), and the rate equals 60 BPM, the first 256 pulses will occur in 0.5 seconds. These will be used by the volume circuit to determine the inspiration waveform rate and ratio. The rest of the pulses up to pulse number 512 will be counted for expiration. From the previous description of ratio circuit 42, at a rate of 60 BPM, a pulse will appear at one second intervals. This pulse occurs at the 512th pulse, thereby cuasing end of expiration and the start of inspiration.

Figure 1E:
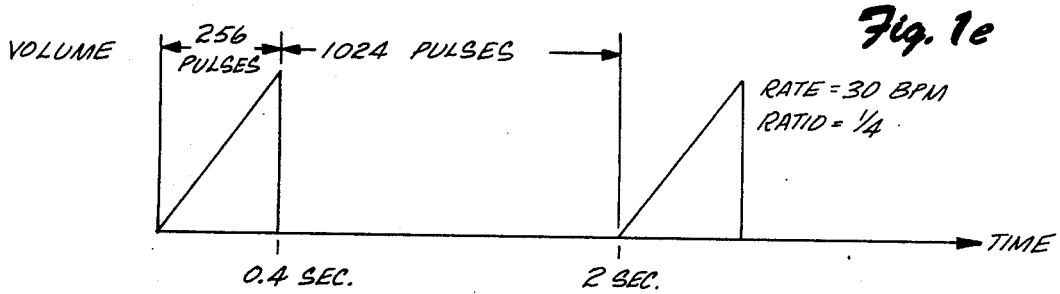

In FIG. 1b the ratio setting "N" = 512 is still the same except that the rate is now 30 BPM, or a pulse every two seconds. The 256 inspiration pulses will take twice as long to occur, but the ratio is still 1/1, because the expiration pulses also take twice as long. In FIG. 1d, the ratio is now ¼ or "N" = 1280. The inspiration pulses are always 256 in number and occur in 0.2 seconds, while the expiration pulses are 1024 in number and occur in 0.8 seconds, so that the ratio is ¼. In FIG. 1e, the rate is decreased to 30 BPM, but the ratio remains fixed. Therefore, rate and ratio independence is maintained.

Figure 5A:
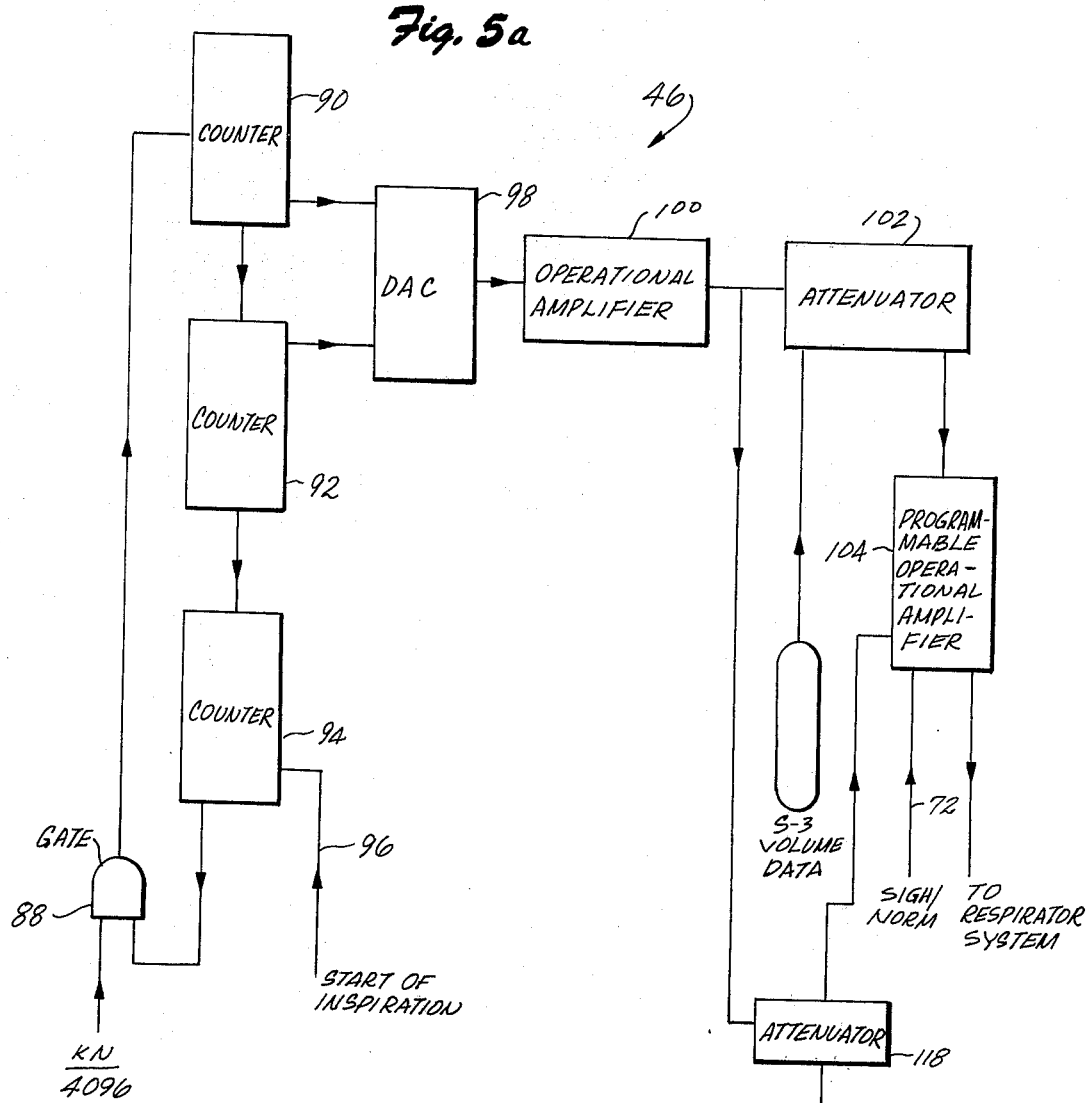
FIG. 5a is a schematic block diagram illustrating a volume signal generating circuit of this invention.
Figure 5B:
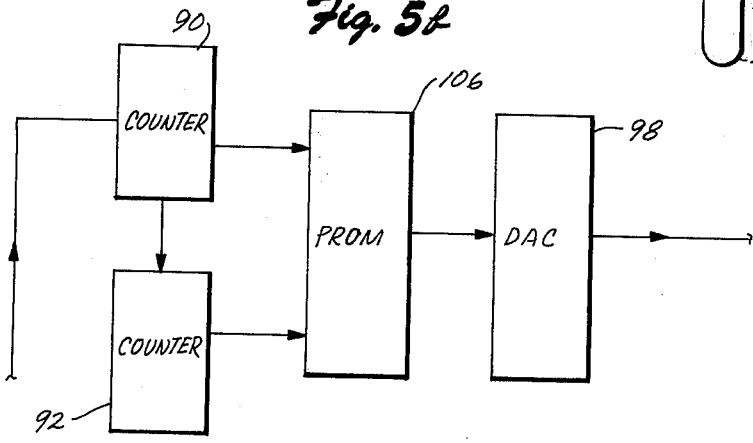

FIG. 5a shows the volume circuit 46 which provides adjustable amplitude waveforms to the respirator drive circuitry. The waveforms are equal to zero during expiration, allowing the piston, or concertina bag apparatus, to return to the start position. The volume circuit includes a gate 88 which performs the "gating on" function for a 256 bit counter consisting of counters 90, 92, and 94. The 256 pulses are gated through when counter 94 has been reset by a start of inspiration signal 96 from the ratio circuit 42. The start of inspiration signal is independent of ratio settings and of any functions in the volume circuit 46. A current output digital-to-analog converter (DAC) 98, in conjunction with an operational amplifier 100, provides a fixed voltage output at the end of inspiration corresponding to 256 pulses. As the counters 92 and 94 accumulate pulses, the DAC 98 provides a linearly increasing ramp from 0 to 10 volts in 256 steps of 40 millivolts (mv) each. These steps are much too small to be discerned by the respirator drive circuits and appear as a smooth analog ramp waveform.

The purpose of switch S-3, which is mechanically linked to an attenuator 102, is to provide independent adjustment of volume. Since the input to the attenuator 102 is always a ramp varying from 0 to 10 volts, the attenuator is essentially a voltage divider that is adjustable in discrete steps of 10 mv. Because the tidal volume is set at 1 volt equal to 1 liter, the operator volume adjustment is calibrated directly in steps of 10 milliliters (ml). The operational amplifier 100 is used to scale the voltage out of the attenuator to the level required by the respirator drive circuits. The output of the amplifier 100 is also fed to the sigh circuit 50. A programmable operational amplifier 104 allows the selection of either sigh or normal volume drive signals to be fed to the respirator drive circuits. This device also allows any increase or decrease in voltage gain required by the respirator drive circuits.

As illustrated in FIG. 1b a PROm 106 can be inserted between the counters 90 and 92, and the DAC 98 so that waveforms other than a simple ramp can be obtained. By proper choice of codes, the PROM 106 can serve as a "look up" table for any of several waveforms.

FIG. 6 shows the sigh function circuit 50 which is designed to periodically provide larger breath of long duration according to the operator controlled switches S-4 through S-7. Rate scalers 108 and 110 provide an output proportional to the settings from a PROM 112. The PROM is pre-programmed to decode operator switch S-5 which an select any sigh rate from 1 to 49 in steps of one. These circuits, in conjuncton with a flip-flop 114, provide a "set" function on the sigh/normal control line 72. The sigh/normal line 72 is used by the rate circuit 38 to switch the PROM address lines from the normal rate switch S-1 to the sigh rate switch S-4. In this way, the rate is changed without affecting any ratio settings. However, the volume settings are changed in the sigh mode. The sigh/normal control line 72 is also fed to the volume circuit 46 (see FIG. 5a) where it is used to control the programmable operational amplifier 104. The operational amplifier 104 selects the drive signal from a sigh attenuator 118 in the sigh circuit 50 which is controlled by operator switch S-7.

A four-bit counter 120, in conjuction with a decoder 122, and operator switch S-6, provide a reset function on the sigh/normal line when the proper number of sighs have been achieved. Switch S-6 may be set for 1, 2 or 3 sighs per interval. An interval is defined as the active sigh time as selected by switch S-5.

Thus, the control system descrbed herein has several advantages over previous electronic systems used in ventilator control. The use of fixed clock and variable rate scalers eliminates problems associated with variable RC oscillators such as non-linearities, instabilities, and drift. This feature provides extremely stable and accurate control of respiratory rate. In addition, field maintenance is simplified because no trim adjustments or calibrations are necessary, and circuit replacements do not require initial adjustments.

The principle of designating a fixed number of counts as inspiration time, and varying the pulse rate to control respiratory frequency, coupled with a variable number of counts for expiration, insures independence of rate and ratio controls. The use of PROM'S provides for easy interfacing between clinical parameters and control signals.

The wide dynamic range necessary in ventilators (5 BPM to 60 BPM) makes the use of RC waveshaping circuits for volume curves impractical when the waveshape must be the same for all rates. This problem is solved by using PROM'S as digital waveform generators capable of generating a large number of frequency-independent waveforms. This solution also avoids problems associated with setting break points and slopes in diode function generators. In addition, an entirely new set of waveforms may be obtained by the substitution of a single integrated circuit. This feature is particularly useful in light of the current controversy regarding the choice of a volume-time waveform which is "best" for a given clinical situation.

In summary, this invention provides a control system for use on ventilators which is time-cycled, has independence of controls, and is stable for variations in patient resistance and compliance. The overall accuracy of all controls has been found to be ±1%.

We claim:

1. A system for digitally controlling an analog waveform signal to be used to control the respiratory cycle of a respirator in which the respiratory cycle has an inspiratory phase and an expiratory phase, the digital system comprising:
   a. means for selecting a first input having a magnitude representative of a predetermined respiratory rate defining the duration for each respiratory cycle;
   b. a digital respiratory rate circuit having means responsive to said first input for producing a first output comprising a series of time pulses having a frequency proportional to the magnitude of said first input;
   c. means for selecting a second input having a magnitude representative of a predetermined respiratory ratio defining the duration of the inspiratory phase relative to the duration of the expiratory phase for each respiratory cycle, the magnitude of the second input being independent of the magnitude of the first input;
   d. a digital respiratory ratio circuit for defining the inspiratory portion of each respiratory cycle, the ratio circuit having means responsive to the second input and to the output of the rate circuit for generating a second output comprising a constant number of timed pulses corresponding to the inspiratory phase of each respiratory cycle in which the portion of each cycle during which said constant number of pulses occur is proportional to said preselected respiratory ratio, and the frequency of said constant number of pulses is proportional to the frequency of pulses generated by the rate circuit, said constant number of pulses being independent of said preselected respiratory rate and ratio; and
   e. means responsive to the output pulses from the respiratory ratio circuit for converting said pulses into an analog waveform signal having magnitude with respect to time which varies in proportion to said preselected respiratory rate and ratio.

2. A digital system according to claim 1 in which the rate circuit includes means for generating a series of timed pulses, and means for modulating the frequency of the timed pulses in proportion to the magnitude of the first input to generate the pulses comprising the output of the rate circuit.

3. A system according to claim 2 in which the rate circuit includes programmable memory means for decoding the first input and producing a first digital signal proportional to the first input, and means responsive to the first digital signal for modulating the frequency of said series of timed pulses in proportion to the magnitude of the first input.

4. A system according to claim 1 in which the first input has a magnitude proportional to a predetermined number of breaths per unit of time; and the rate circuit includes means for converting the magnitude of the first input into an output comprising a series of pulses having a frequency proportional to said predetermined number of breaths per unit of time.

5. The system according to claim 4 in which the rate circuit includes means for generating a series of time pulses, and means for modulating the frequency of the time pulses in proportion to the magnitude of the first input to produce an output comprising a series of pulses having a frequency proportional to said predetermined number of breaths per unit of time.

6. The system according to claim 1 in which the ratio circuit includes means responsive to the second input for generating a series of timed pulses prepresenting the inspiratory and expiratory phase of each respiratory cycle, and in which the number of said pulses corresponding to the inspiratory phase is constant, and the number of pulses corresponding to the expiratory phase is a multiple of said constant number which varies in magnitude in direct proportion to the duration of the expiratory phase compared with that of the inspiratory phase; and further including means responsive to the pulses generated by the rate circuit for setting the frequency of the series of pulses generated by the ratio circuit for each inspiratory cycle in proportion to the frequency of the pulses generated by the rate circuit.

7. The system according to claim 6 in which the ratio circuit further includes means responsive to the frequency of pulses from the output of the rate circuit to generate a series of reset pulses of uniform frequency representing the beginning of each respiratory cycle; and in which the analog waveform producing means is activated by said reset pulses to initiate said analog waveform at the beginning of each respiratory cycle.

8. The system according to claim 6 in which the ratio circuit includes programmable memory means for decoding the second input and producing a second digital signal proportional to said preselected respiratory ratio; and means responsive to said second digital signal to determine the number of said pulses occurrring during each respiratory cylce, and means responsive to the pulses from the rate circuit for adjusting the frequency of said number of pulses to be generated during each respiratory cycle.

9. The system according to claim 8 in which the ratio circuit further includes means responsive to the frequency of pulses from the output of the rate circuit to generate a series of reset pulses of uniform frequency representing the beginning of each respiratory cycle; and in which the analog waveform producing means is activated by said reset pulses to initiate said analog waveform at the beginning of each respiratory cycle.

10. The system according to claim 1 in which the analog waveform producing means includes means for counting only the constant number of pulses generated by the respiratory ratio circuit; and in which the means for generating said analog waveform produces an electrical output of a predetermined magnitude in response to each pulse counted by the counting means.

11. The system according to claim 10 including a digital-to-analog-converter to generate said analog waveform in response to the counted pulses.

12. The system according to claim 10 including means for selecting a third input having a magnitude representative of a predetermined volume of gas to be delivered by the respirator during the inspiratory phase of each respiratory cycle; and means responsive to said third input for modulating the magnitude of said analog waveform signal in proportion to the magnitude of the third input.

13. The system according to claim 1 in which the analog waveform producing means includes means for counting only said constant number of pulses corresponding to the inspiratory phase of each respiratory cycle; programmable memory means to modulate the magnitude of the counted pulses in accordance with a preselected waveform having a programmable magnitude with respect to time; and means for generating an analog output waveform having a magnitude with respect to time throughout each inspiratory phase which is proportional to the magnitude of the pulses counted by the counting means.

14. The system according to claim 7 in which the analog waveform producing means includes means for counting only said constant number of pulses corresponding to the inspiratory phase of each respiratory cycle; and means responsive to the reset pulses to generate said waveform signal at the beginning of each inspiratory phase; and in which each generated waveform has a predetermined magnitude with respect to time determined by the magnitude of the pulses counted by the counting means.

15. The system according to claim 10 including means for selecting a third input having a magnitude representative of a predetermined volume of gas to be delivered by the end of each inspiratory phase; and in which the analog waveform generating means is responsive to said third input to generate an analog waveform signal having a magnitude with respect to time during each inspiratory phase representative of said predetermined volume of gas being delivered at said preselected respiratory rate and ratio.

16. The system according to claim 15 in which the analog waveform producing means further includes means for counting only said constant number of pulses corresponding to the inspiratory phase of each respiratory cycle; and in which the analog signal generated in response to the counted pulses is modulated in proportion to the magnitude of the third input.

17. The system according to claim 1 including a sigh rate circuit having means for selecting a fourth input having a magnitude representative of a predetermined duration for a sigh respiratory cycle; means for overriding the rate circuit output to generate a series of time pulses having a frequency proportional to the preselected duration of the sigh cycle; means for allowing the ratio circuit to respond to the pulses generated by the sigh rate circuit in place of the pulses generated by the rate circuit; and means for selectively terminating operation of the overriding means.

18. The system according to claim 17 including means for generating a fifth input having a magnitude representative of a predetermined sigh volume of gas to be delivered by the end of each sigh respiratory cycle; and including means responsive to said fifth input to adjust the magnitude of said analog waveform signal with respect to time in proportion to the magnitude of said fifth input.

19. A digitally controlled respirator system for delivering a controlled volume of gas to a patient comprising:
   a. gas delivery means for being positioned periodically to force a volume of gas under pressure into the lungs of a patient throughout an inspiratory period of a respiratory cycle;
   b. drive means operatively connected to the gas delivery means to displace said volume of gas;

c. a digital waveform generating system for producing an analog waveform signal to control positioning of the gas delivery means throughout the inspiratory and expiratory phase of each respiratory cycle of the gas delivery means, the digital system comprising:
   1. means for selecting a first input having a magnitude representative of a predetermined respiratory rate defining the duration for each respiratory cycle,
   2. a digital respiratory rate circuit having means responsive to said first input for producing a first output comprising a series of timed pulses having a frequency proportional to the magnitude of said first input,
   3. means for selecting a second input having a magnitude representative of a predetermined respiratory ratio defining the duration of the inspiratory phase relative to the duration of the expiratory phase for each respiratory cycle, the magnitude of the second input being independent of the magnitude of the first input,
   4. a digital respiratory ratio circuit for defining the inspiratory portion of each respiratory cycle, the ratio circuit having means responsive to the second input and to the output of the rate circuit for generating a second output comprising a constant number of timed pulses corresponding to the inspiratory phase of each respiratory cycle in which the portion of each cycle during which said constant number of pulses occur is proportional to said preselected respiratory ratio, and the frequency of said constant number of pulses is proportional to the frequency of pulses generated by the rate circuit, said constant number of pulses being independent of said preselected respiratory rate and ratio, and
   5. means responsive to the output pulses from the respiratory ratio circuit for converting said pulses into an analog waveform signal having a magnitude with respect to time which varies in proportion to said preselected respiratory rate and ratio; and
d. means for applying the waveform signal to the respirator drive means to deliver said inspiratory volume of gas to the patient at said preselected respiratory rate and ratio.

20. The system according to claim 19 in which the analog signal generating means includes means for selecting a third input signal having a magnitude representative of a predetermined volume of gas to be delivered by the end of each inspiratory phase, and means responsive to said third input for modulating the magnitude of said analog waveform signal in proportion to the magnitude of the third input.

21. The system according to claim 20 in which the digital waveform generating system comprises means for generating a reference signal representing variations in the position of the gas delivery means with respect to time throughout the inspiratory period necessary to deliver a desired volume of gas in accordance with a desired volume-versus-time waveform; and further including closed loop feedback means for controlling the instantaneous position of the gas delivery means throughout the inspiratory period, the closed loop feedback means including:
   1. first means responsive to the actual position of the gas delivery means for generating a position feedback signal representing the actual volume of gas displaced by the gas delivery means with respect to time throughout the inspiratory period,
   2. second means responsive to said reference signal and said position feedback signal for providing, throughout the inspiratory period, a position error signal representing the deviation between the instantaneous desired position and the corresponding actual position of the gas delivery means, and
   3. third means for applying said position error signal to the drive means for adjusting the instantaneous position of the gas delivery means in proportion to said error signal throughout the inspiratory period to deliver gas to the patient in accordance with the desired volume-versus-time waveform.

22. The system according to claim 21 in which the drive means comprises a translational motor having an input for being converted into translational motion of an output shaft of the motor for linearly positioning the gas delivery means to displace the volume of gas to be delivered.

23. A system for digitally controlling an analog waveform signal to be used to control the respiratory cycle of a respirator in which the respiratory cycle has an inspiratory phase and an expiratory phase, the digital system comprising:
   a. means for selecting a first input having a magnitude representative of a predetermined respiratory rate defining the duration for each respiratory cycle;
   b. a digital respiratory rate circuit having means responsive to said first input for producing a first output comprising a series of timed pulses having a frequency proportional to the magnitude of said first input;
   c. means for selecting a second input having a magnitude representative of a predetermined respiratory ratio defining the duration of the inspiratory phase relative to the duration of the expiratory phase for each respiratory cycle;
   d. a digital respiratory ratio circuit having means responsive to the second input and to the output of the rate circuit for generating a predetermined number of timed pulses representative of each respiratory cycle, in which the number of pulses corresponding to the inspiratory phase of each cycle is constant, and the number of pulses corresponding to the expiratory phase is a multiple of said constant number of pulses which varies in proportion to said preselected respiratory ratio; and means for setting the frequency of said predetermined number of pulses for each respiratory cycle in proportion to the frequency of the pulses generated by the rate circuit; said constant number of pulses being independent of said preselected respiratory rate and ratio; and
   e. means for generating an analog waveform signal in response to the output pulses from the ratio circuit, the waveform generating means including means for counting only said constant number of output pulses representative of the inspiratory phase of each respiratory cycle, means for generating a third input signal having a magnitude representative of a predetermined volume of gas to be delivered during the inspiratory phase of each respiratory cycle, and means responsive to the third input signal and to the pulses counted by the counting means to convert said constant number of pulses into an analog waveform signal having a magnitude proportional to that of the third input defining said predetermined inspiratory volume of gas being delivered by the respirator at said preselected respiratory rate and ratio.

24. The system according to claim 23 including means responsive to the frequency of pulses from the output of the rate circuit to generate a series of reset pulses of a uniform frequency representing the beginning of each respiratory cycle; and in which the analog waveform producing means is activated by said uniform frequency reset pulses to initiate said analog waveform at the beginning of each respiratory cycle.

25. The system according to claim 23 in which the respiratory rate circuit includes means for generating a series of timed pulses, and means for modulating the frequency of the timed pulses in proportion to the magnitude of the first input to generate the pulses comprising the output of the rate circuit.

26. The system according to claim 25 in which the rate circuit includes programmable memory means for decoding the first input and producing a first digital signal proportional to the first input, and means responsive to the first digital signal for modulating the frequency of said series of time pulses in proportion to the magnitude of said first input.

27. The system according to claim 23 in which the first input is in breaths per unit of time, and the rate circuit includes means for converting the magnitude of the first input into an output comprising a series of pulses having a frequency proportional to said preselected number of breaths per unit of time.

28. The system according to claim 23 in which the ratio circuit includes programmable memory means for decoding the second input signal and producing a corresponding second digital signal proportional to said respiratory ratio; and means responsive to said second digital signal to determine the number of said pulses occurring during each respiratory cycle; and in which the means responsive to the pulses from the rate circuit adjusts the frequency of said number of pulses to be generated during each respiratory cycle.

29. The system according to claim 23 including means for modulating the magnitude of the analog waveform with respect to time throughout the inspiratory phase of each cycle.

30. The system according to claim 29 in which the modulating means comprises programmable memory means to modulate the magnitude of the counted pulses in accordance with a predetermined waveform having a programmable magnitude defining a predetermined volume of gas to be delivered with respect to time of inspiration; and including means for generating an analog waveform having a magnitude with respect to time which is proportional to the time-varying magnitude of the pulses counted by the counting means.

31. The system according to claim 30 including means responsive to the frequency of pulses generated by the rate circuit to generate a series of reset pulses of uniform frequency representing the beginning of each respiratory cycle; and in which the counting means is activated by said reset pulses to initiate said analog waveform at the beginning of each respiratory cycle.

* * * * *

UNITED STATES PATENT AND TRADEMARK OFFICE
CERTIFICATE OF CORRECTION

PATENT NO. : 4,001,700
DATED : January 4, 1977
INVENTOR(S) : Albert M. Cook et al It is certified that error appears in the above–identified patent and that said Letters Patent are hereby corrected as shown below:

Col. 5, line 6, "present" should be -- preset --.
Col. 6, line 2, "inspriation" should be -- inspiration --;
      line 4, "of" should be -- is --;
      line 27, "cuasing" should be -- causing --.
Col. 7, line 11, "1b" should be -- 5b --;
      line 11, "PROm" should be -- PROM --;
      line 22, "an" should be -- can --.
Col. 9, line 12, "prepresenting" should be -- representing --;
(claim 6)
      line 38, "occurrring" should be -- occurring --;
      line 39, "cylce" should be -- cycle --

Signed and Sealed this

Tenth Day of May 1977

[SEAL]

Attest:

RUTH C. MASON
*Attesting Officer*

C. MARSHALL DANN
*Commissioner of Patents and Trademarks*